(12) United States Patent  (10) Patent No.: US 8,389,892 B2
Hinrichs et al.  (45) Date of Patent: Mar. 5, 2013

(54) X-RAY MICROSCOPY FOR CHARACTERIZING HOLE SHAPE AND DIMENSIONS IN SURGICAL NEEDLES

(75) Inventors: Eric Hinrichs, Pipersville, PA (US); Robert E. Maurer, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 959 days.

(21) Appl. No.: 12/469,279

(22) Filed: May 20, 2009

(65) Prior Publication Data

US 2010/0294747 A1  Nov. 25, 2010

(51) Int. Cl.
*B23K 26/00* (2006.01)

(52) U.S. Cl. ............ 219/121.71; 219/121.7; 219/121.83

(58) Field of Classification Search ................ 219/121.7, 219/121.71, 121.83, 121.65
See application file for complete search history.

(56) References Cited

U.S. PATENT DOCUMENTS

| | | | |
|---|---|---|---|
| 3,390,769 A | 7/1968 | Tatham et al. | |
| 4,600,998 A * | 7/1986 | Huet | 702/40 |
| 4,695,729 A | 9/1987 | Monno | |
| 4,910,377 A * | 3/1990 | Matsutani et al. | 219/121.19 |
| 5,241,419 A * | 8/1993 | Pratt et al. | 359/634 |
| 5,438,746 A | 8/1995 | Demarest | |
| 5,473,810 A | 12/1995 | Demarest | |
| 5,477,609 A | 12/1995 | Demarest | |
| 5,485,668 A | 1/1996 | Demarest | |
| 5,487,212 A | 1/1996 | Demarest | |
| 5,487,216 A | 1/1996 | Demarest | |
| 5,487,308 A | 1/1996 | Demarest | |
| 5,495,420 A | 2/1996 | Demarest | |
| 5,500,991 A | 3/1996 | Demarest | |
| 5,539,973 A | 7/1996 | Smith | |
| 5,630,268 A | 5/1997 | Smith | |
| 5,644,834 A | 7/1997 | Smith | |
| 5,661,893 A | 9/1997 | Smith | |
| 5,701,656 A | 12/1997 | Smith | |
| 5,776,268 A | 7/1998 | McJames | |
| 5,793,634 A | 8/1998 | Demarest | |
| 5,844,142 A | 12/1998 | Blanch | |
| 5,873,212 A | 2/1999 | Esteves | |
| 5,911,449 A | 6/1999 | Daniele | |
| 5,915,751 A | 6/1999 | Esteves | |
| 5,918,284 A | 6/1999 | Blanch | |
| 5,920,482 A | 7/1999 | Demarest | |
| 5,937,504 A | 8/1999 | Esteves | |
| 6,012,216 A | 1/2000 | Esteves | |
| 6,016,682 A | 1/2000 | Tannhauser | |
| 6,018,860 A | 2/2000 | Smith | |
| 6,032,343 A | 3/2000 | Blanch | |
| 6,081,981 A | 7/2000 | Demarest | |
| 6,163,948 A | 12/2000 | Esteves | |
| 6,252,195 B1 | 6/2001 | Mosavi | |
| 6,263,558 B1 | 7/2001 | Blanch | |
| 6,600,806 B1 | 7/2003 | Istar | |
| 7,185,411 B2 | 3/2007 | Lenihan | |
| 7,638,732 B1 * | 12/2009 | Dobbs | 219/121.7 |
| 7,909,507 B2 * | 3/2011 | Bunker et al. | 374/121 |
| 2005/0109741 A1 | 5/2005 | Carney | |
| 2005/0113869 A1 | 5/2005 | Price | |

FOREIGN PATENT DOCUMENTS

JP  8271444 A  10/1996

* cited by examiner

*Primary Examiner* — Mark Paschall
(74) *Attorney, Agent, or Firm* — E. Richard Skula

(57) ABSTRACT

A novel method of characterizing laser drilled boreholes is disclosed. The method uses x-ray microscopy for dimensional characterization. The x-ray output may be processed to control manufacturing equipment in automated production systems, including laser drilling systems and swaging apparatus.

20 Claims, 14 Drawing Sheets

X-RAY MICROSCOPY FOR CHARACTERIZING HOLE SHAPE AND DIMENSIONS IN SURGICAL NEEDLES

TECHNICAL FIELD

The field of art to which this invention relates is x-ray microscopy, in particular, x-ray microscopy for use with surgical needles and surgical needle manufacturing processes.

BACKGROUND OF THE INVENTION

Surgical needle and suture combinations are well known in the surgical arts. Surgical needles and sutures are a fundamental mainstay of surgical procedures and trauma repair. Surgical sutures are conventionally woven or braided from natural or synthetic polymeric materials including silk, polyesters, polydioxanone, polylactide, and the like. The sutures may also be constructed from a monofilament. The sutures may be bioabsorbable or nonabsorbable.

Surgical sutures are typically mounted to conventional surgical needles to create a needle and suture combination for use by the surgeon to approximate tissue, etc. A conventional surgical needle is typically an elongated, curved structure having a distal piercing tip and a proximal suture mounting section. The needles may optionally have cutting edges to assist in tissue penetration. The proximal suture mounting sections may have conventional blind boreholes or channels for receiving the end of a suture. One or both ends of a surgical suture may be mounted in the channel or borehole and secured therein in a conventional manner, including conventional mechanical swaging in which the suture mounting end of the surgical needle is partially compressed, as well as adhesives, cements, etc. Surgical needles are conventionally made from biocompatible materials, especially metals and metal alloys such as surgical grade stainless steels.

Early in the development of surgical needles, channels were used to attach suture to the needle. This was an improvement over needles having eyelets wherein a suture was threaded through the eyelet in the field. However, channels, when closed (i.e., swaged), create a bump (to a lesser or greater degree) in the distal portion of the channel. Such bumps may be undesirable to surgeons and other medical professionals since a bump may disrupt the smooth passage of the needle through tissue. This characteristic of channeled needles was eliminated with the introduction of mechanically drilled boreholes for suture mounting, however mechanical drilling can only be utilized for low strength alloys and large diameter holes. The relatively recent utilization of laser drilling was an important advancement in this art and addresses this issue as it allows small diameter boreholes to be drilled in small diameter wires, especially wires made from high strength alloys, which are currently off-limits for the most part to mechanical drilling due to technological limitations.

Drilled boreholes in surgical needles are particularly desirable since the profile of the needle body is not altered in the same manner as when a channel is punched into the proximal suture mounting end of the needle. A smooth profile is desirable to the surgeon since it is believed to reduce tissue trauma and to reduce the force required to pull the needle through tissue with a commensurate reduction in drag. Drilled boreholes in surgical needles may be produced in a number of conventional manners. Two conventional methods used to drill boreholes, as previously mentioned, include mechanical drilling and laser drilling.

There are distinct differences between mechanically drilled and laser drilled boreholes. Mechanically drilled boreholes are typically uniform and precise in shape and profile as they take on the shape of the drill. Mechanically drilled surgical needles are easily inspected using conventional plug gages (i.e., machined cylindrical members having a constant diameter or, optionally, tapering from proximal to distal). Although mechanical drilling will typically produce a borehole having relatively precise dimensions and a precise configuration, there are several disadvantages that may be associated with mechanical drilling. These include slow drilling speeds in an automated high speed manufacturing system, drill wear and life, the difficulty in manufacturing production grade drills for needles having fine wire sizes, increased costs, and the inability to drill small diameter holes in high strength alloys in small wire sizes Although laser drilling overcomes these problems, laser drilled holes, on the other hand, pose several other unique problems, although certainly manageable, that have yet to be addressed. Laser drilled needles tend to have several issues associated with the use of a laser to drill a borehole. For example, in cases where the laser melts the material to form the hole, there is the potential for recast to form on the interior of the hole, and such recast may affect suture attachment. Other issues may include the consistency of the borehole profile and the smoothness of the borehole, as well as the possibility of blow-outs.

Laser drilling processes have been developed for drilling boreholes in surgical needles. Examples of such processes are included in the following U.S. patents and patent application, which are incorporated by reference: U.S. Pat. No. 6,018,860, 5,776,268, 5,701,656, 5,661,893, 5,644,834, 5,630,268, 5,539,973, 6,252,195, and US20050109741. Such laser drilling processes have many advantages, including adaptability for high speed manufacturing processes, efficiencies and cost, the ability to drill small holes in small wire diameters in substantially any material, and reduced maintenance.

Although laser drilling processes have all of these advantages, as previously mentioned the boreholes drilled by lasers typically do not have the same precise dimensional configuration as mechanically drilled boreholes. Laser drilling utilizes a conventional laser that emits a laser beam, which is typically tapered or Gaussian, in shape. This means that the bore hole drilled by the laser beam is typically tapered as it gets deeper. The laser beam used for drilling is engineered with respect to parameters such as energy level, pulse, waveform, etc., to produce a borehole having a desired configuration and characteristics including borehole depth, length, cross-section, and orientation about the longitudinal axis of the needle and about the center of the needle wire body, such that the laser drilled borehole is capable of sufficiently and effectively accepting an end of a surgical suture for mounting and affixation.

This is the result of the very nature of laser drilling wherein a high energy, pulsed laser beam essentially liquefies or vaporizes the target metal in the proximal, suture-mounting end of the needle upon which the beam is directed. In some laser drilling, the molten material will reform inconsistently within the hole; this reformed material is commonly called recast, as mentioned previously. The recast can create a non-uniform hole condition which may affect suture insertion and attachment.

In order to effectively affix or mount the end of a surgical suture in a laser-drilled borehole in a surgical needle, the borehole should have a substantially uniform diameter, similar to a bore hole produced in a mechanically drilled needle, albeit tapered as mentioned above. Similarly, the length of the borehole must have maximum and minimum dimensions. A length that is too long may weaken the needle, while too short may result in needle/suture separation. And, the borehole must be relatively centered about the longitudinal axis of the proximal end of the suture needle.

The present state of the art with respect to the measurement of the dimensions of laser-drilled boreholes is to use conventional mechanical pin gages, as is the conventional standard for mechanically drilled boreholes. The use of pin gages is typically a manual procedure wherein statistically significant quantities of needles are selected from lots of drilled needles, and the pin gages are manually inserted by an inspector into the drilled boreholes. The resulting data is recorded. There are several disadvantages associated with the use of mechanical pin gages. While pin gages are ideally suited for mechanically-drilled needles, they are not especially suitable for laser drilled needle manufacturing for several reasons. First of all, pin gages are not adapted for use in high speed manufacturing processes. Also, the pin gages used to measure very small diameter boreholes are expensive and difficult to manufacture, and for the finer diameters are easily damaged. In addition, the use of pin gages will not provide information with respect to the presence of re-cast. Pin gages can easily measure a mechanically-drilled borehole as it is cylindrical in nature and has a regular profile, but a laser drilled borehole in a surgical needle is not typically cylindrical in profile and may contain re-cast and varying diameters along the length of the borehole. Thus, a pin gage can only approximate the minor diameter measurement of a laser drilled borehole, and provides no other information with respect to other important parameters such as taper, length, degree of centeredness, irregularities, degree of skewing, etc. The presence of re-cast may cause a misrepresentation of the true minor diameter of the laser drilled hole. Further, as mentioned above, the pin gage measurements fail to address potential variants in the borehole profile. The use of a pin gage does not indicate the major diameter or provide a representation of the variation in the borehole profile. Therefore the only measurement a pin gage can provide is an indication of the smallest potential diameter of the borehole, without a value or determination of variations in diameter, profile, degree of skewedness, and other critical parameters.

Another disadvantage associated with the use of pin gages is that pin gages do not provide real time data that can be used to immediately adjust production-processing parameters. Statistical sampling of a batch of drilled needles may indicate that the boreholes are out of specification, requiring the destruction of an entire out-of-specification batch of needles. Other disadvantages include: pin gage wear, whether the gage is a minus or plus in tolerance with respect to the required borehole measurement, and acceptance of boreholes that meet the pin gage criteria, but have undetected internal geometries that inhibit, or preclude subsequent suture attachment. Pin gage measuring is a manual process and, consequently, is not a procedure that can keep pace with a high speed surgical needle manufacturing processes required in modern needle manufacturing processes and typically associated with laser drilling. Statistical sampling of laser drilled needles, although possible, if one were willing to accept any attendant disadvantages, is potentially prohibitive and it would not be possible to inspect a statistically relevant sample in real-time. Therefore it is typically necessary to use a reduced sample size, which may lead to false positives, possibly resulting in the destruction of laser drilled needles that, if inspected at acceptable levels, would not result in such a loss and the commensurate expense associated with the loss of a production batch of needles. Another disadvantage of pin gage inspection methods includes the possible acceptance of boreholes that meet the pin gage criteria, but have undetected defects, internal geometries or configurations that inhibit, or preclude subsequent effective suture insertion and attachment, possibly resulting in failures in the field.

As discussed above, the conventional means of measurement for drilled boreholes, i.e., plug gaging, does not work well with laser drilled holes because of the numerous attendant disadvantages. Given the inconsistent profile of a laser hole, plug gaging only can provide the user with an indication of the minor diameter of the inconsistent profile, but fails to provide a measure of the major diameter and/or the hole profile. This is a serious drawback, as variation on the hole profile and the differences between the minor and major hole diameters directly affects the ability to secure the suture to the needle. In mechanically drilled holes this is not a factor as the hole is a reflection of the drill geometry. Another drawback is that pin gaging is extremely time-consuming and only as accurate as the pin gage is manufactured and maintained. Unfortunately, there are no options available other than physical destruction, specifically, mechanically cross-sectioning a needle and examining the shape of the borehole, which is difficult, laborious, time consuming, and not cost-effective to do with a statistically significant sample size, and does not provide real time information which can be used to control production processes.

Therefore, there is a need in this art for novel methods of characterizing drilled boreholes in a high speed manufacturing environment and using such characterizations to adjust and control laser drilling and subsequent manufacturing processes. The significant benefit of which is to improve yields, product performance, and improve product consistency.

SUMMARY OF THE INVENTION

Accordingly, a novel method of characterizing drilled boreholes in surgical needles is disclosed. In this method, an x-ray beam is directed from an x-ray generator at a surgical needle, preferably the proximal end of a surgical needle containing a drilled borehole. An image of the proximal end of the needle is digitally generated from a sensor, which the x-ray beam impinges upon. At least the proximal end of the needle is located between the x-ray generator and the sensor. The image includes the laser-drilled borehole. The digital image is processed to determine a deviation from a standard dimensional specification for the borehole. It is particularly preferred that the borehole be laser drilled.

Another aspect of the present invention is a method of controlling a laser drilling apparatus during a borehole drilling process. In this method, a laser is provided that emits a laser beam at the proximal end of a surgical needle to drill a borehole therein. An x-ray beam is directed from an x-ray generator at a surgical needle, preferably the proximal end of a surgical needle containing the laser-drilled borehole. An image of the proximal end of the needle is digitally generated from a sensor, which the x-ray beam impinges upon. At least the proximal end of the needle is located between the x-ray generator and the sensor. The image includes the laser-drilled borehole. The digital image is processed to determine a deviation from a standard dimensional specification for the borehole. Then an algorithm is provided to determine the appropriate corrections to the parameters for the laser beam to provide for a drilled bore hole in the surgical needles that is within the specification.

Yet another aspect of the present invention is a method of characterizing laser-drilled boreholes in surgical needles. In this method, an x-ray beam is directed from an x-ray generator at the surgical needle, preferably the proximal end of a surgical needle containing a laser-drilled borehole. An image of the proximal end of the needle is digitally generated from a sensor, which the x-ray beam impinges upon. At least the proximal end of the needle is located between the x-ray generator and the sensor. The image includes the laser-drilled borehole. The digital image is processed to determine a deviation from a standard dimensional specification for the borehole and to determine the measurements of the borehole. The needle or a carrier strip carrying the needle is marked with a code containing the measurements of the image, and each needle is provided with a digital identity.

Optionally, downstream process steps can utilize this information to control the attachment of the suture in the drilled boreholes by varying compression variables such as pressure, time, and dwell to compensate for subtle changes in the borehole profile as determined by the x-ray analysis. This greatly contributes to the consistency and efficacy of the suture/needle interface or attachment and directly contributes to the performance of the component, These and other aspects and advantages of the present invention will become more apparent from the following description and accompanying drawings.

DETAILED DESCRIPTION OF THE INVENTION

Figure 2:
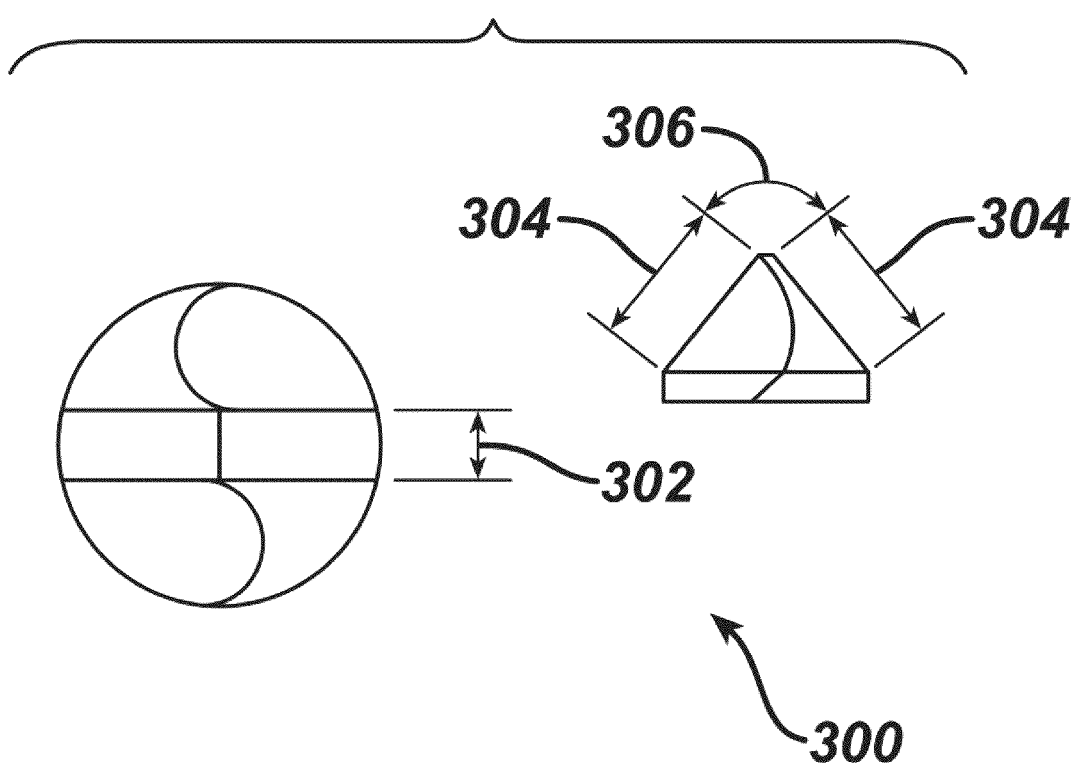
FIG. 2 is a schematic illustrating the geometric characteristics and parameters of a mechanical drill

The terms "surgical needle" and "needle" are used interchangeably herein. There is a general recognition in the art of surgical needle manufacturing that a laser drilled borehole diameter is not as consistent as a mechanically drilled borehole. In mechanically drilled boreholes, the drill defines the borehole diameter whereas in laser drilling, the focus and energy and other known characteristics of the laser beam control the hole diameter. For mechanical drills, the geometry of the drill is very important with respect to borehole accuracy, especially the flute length and flute symmetry of the mechanical drill. FIG. 2 identifies and illustrates key drill geometrical characteristics of a mechanical drill 300, including web width 302, flute length 304, included angle 306, and symmetry. Since a borehole diameter is physically defined by the drill, pin gaging a resulting mechanically drilled borehole in a surgical needle is appropriate as a testing means, since the drill will, both theoretically and practically, drill consistently throughout the depth of the borehole. Pin gaging will indicate nonconformities such as off specification diameter or even out of round boreholes caused for example by a flexing drill, worn or broken drill, or flexing needle.

Figure 3:
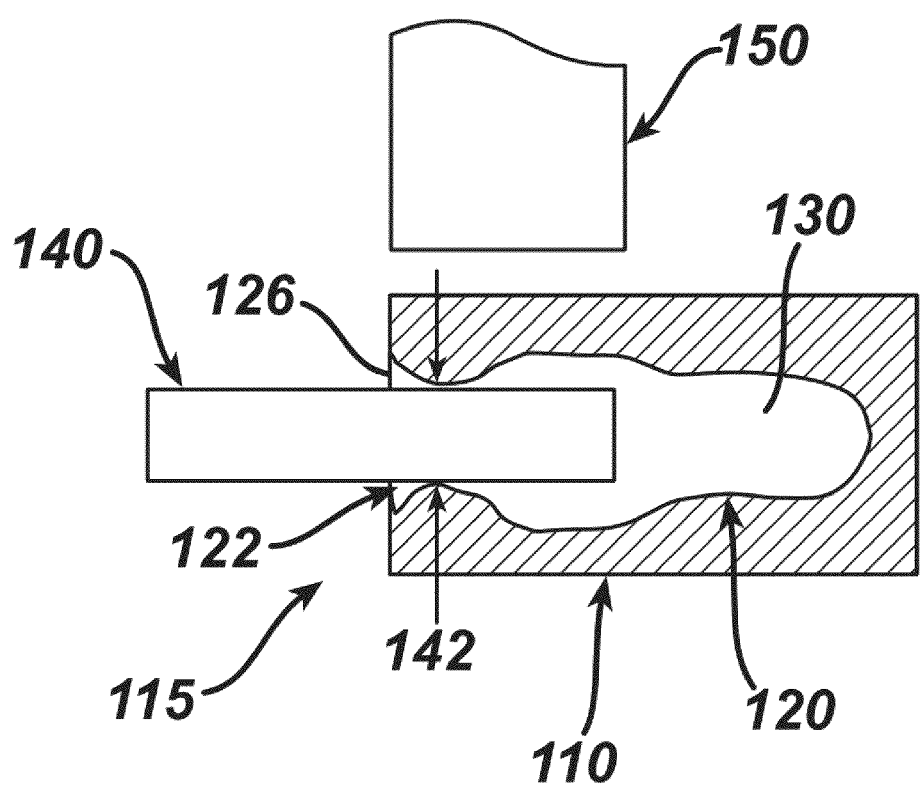
FIG. 3 is a schematic of a pin gage inserted into a borehole of a laser drilled surgical needle; the needle is illustrated in cross-section.

As mentioned above, in laser drilling the focus and energy of the beam, along with other parameters, are critical to borehole diameter consistency, as well as depth and other parameters of the shape of the hole. Variations in diameter are detrimental to accurate borehole gaging and attachment. If the diameter varies, pin gaging will only allow the inspector to ascertain the diameter of the smallest diameter; this precludes measurement of the greater diameter. Consequently, an inaccurate evaluation of hole diameter is obtained over the length of the swage area (see FIG. 3) when pin gaging is employed for diameter measurement. As illustrated in FIG. 3, the proximal end 115 of a surgical needle 110 is seen to have a laser drilled bore hole 120 having proximal opening 122, end 126 and elongated cavity 130. The cavity 130 is seen to have several diameters along its length. The pin gage 140 inserted into bore hole 120 is only capable of determining the minimum diameter 142 of the bore hole cavity 140. Also illustrated is one section of a swage die 150.

Figure 4:
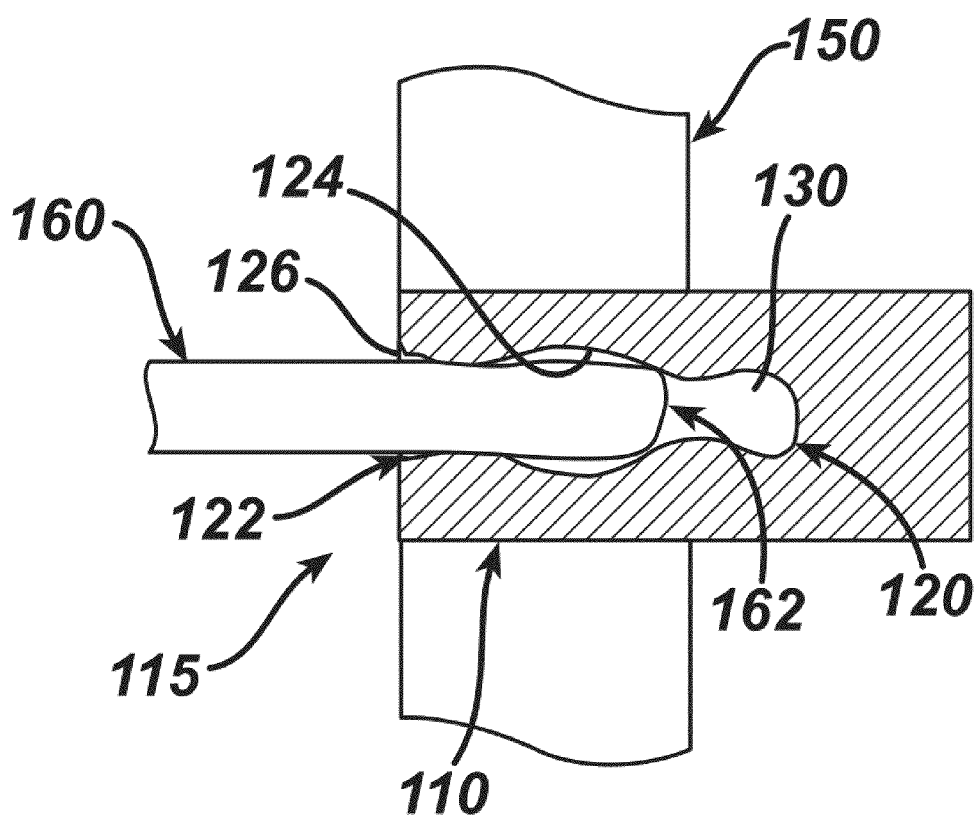
FIG. 4 is a schematic showing the distal end of a surgical suture mounted and swaged in a laser drilled borehole in the proximal end of a surgical needle.
Figure 5:
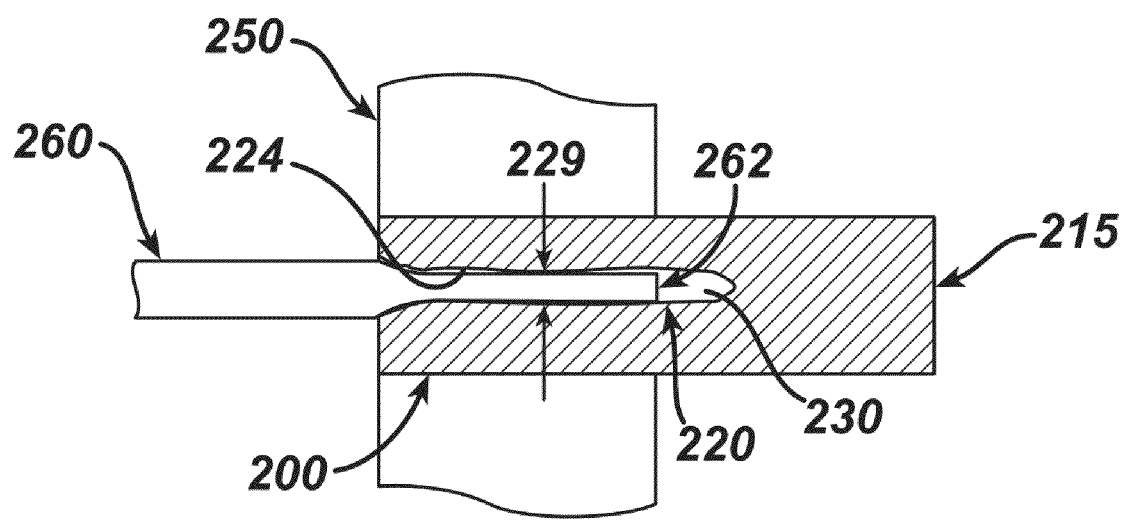
FIG. 5 is a schematic illustrating the distal end of a surgical suture swaged into a mechanically drilled borehole in the proximal end of a surgical needle.

The attachment concern with borehole diameter variation associated with laser drilling (i.e., varying diameter along the longitudinal length of the borehole) is related to the nature of the swaging process. Swaging is conventionally based upon fixed displacement, and this means that the swaging dies will close to the same point each time. Any variation in suture diameter, suture density, needle barrel diameter, or borehole diameter will affect attachment strength values. This is illustrated in FIG. 4. As seen in FIG. 4, the surgical needle 110 has proximal end 115. The needle has laser drilled longitudinal borehole 120 having proximal opening 122, end 126 and elongated cavity 130. A distal end 162 of a suture 160 is seen to be inserted in cavity 130 through opening 122. Swage die members 150 are seen to be located on either side of the proximal end 115 of needle 110. Due to the irregular shape of bore hole cavity 130, it is not possible to completely insert the end 162 of suture 160 into cavity 130. This is due to the irregularly formed shape of the laser drilled borehole 120 having various minor and major dimensions along the length of the cavity 130. When mechanically swaged by swage members 150, the sides 124 of the bore hole 120 will not uniformly engage and compress suture end 162 along its length, potentially compromising retention in the borehole 120. A needle 200 having a mechanically drilled bore hole 220 is illustrated in FIG. 5. The borehole 220 is seen to have cavity 230 having a uniform or substantially constant diameter 229. The distal end 262 of suture 260 is seen to be completely emplaced within borehole 220 and uniformly engaged by sides 224 when the end 215 of needle 200 is mechanically swaged by swage die members 250.

If the borehole diameter of a laser drilled borehole can be controlled in a consistent regular manner, similar to a mechanically drilled needle, the consistency of pull values of attached sutures from boreholes and improvement in yields will be significant. The presence of recast will affect borehole measurements in laser-drilled needles. Recast is a phenomenon wherein the melted material reforms in the hole and alters the intended shape of the hole as a consequence. It is sometimes difficult to isolate recast and can result in a smaller measurement and the impression that the hole diameter is smaller than it actually is.

Figure 6:
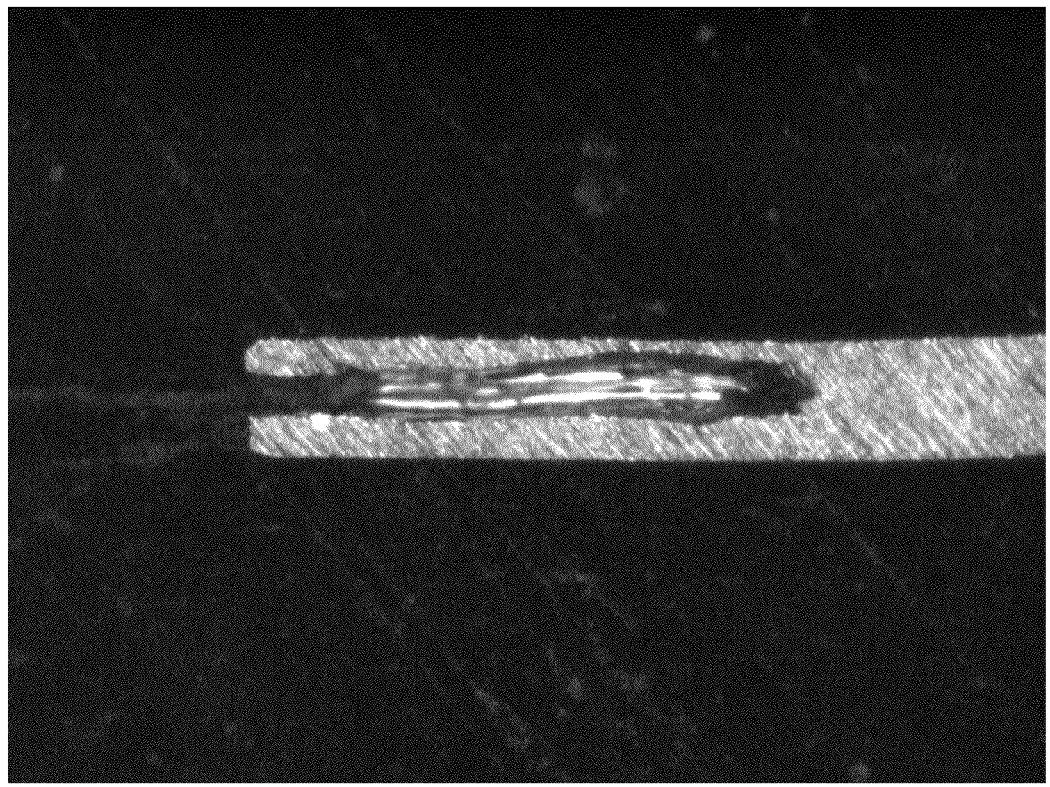
FIG. 6 is a photograph of a mounted and cross-sectioned laser drilled surgical needle showing the borehole.

FIG. 6 is a photograph of a mounted, and cross-sectioned, laser-drilled needle. It clearly shows why pin gaging is disadvantageous and impractical with laser-drilled needles in that the accuracy of the testing varies with the degree of trueness of the laser-drilled borehole. It is apparent and can be seen that the borehole cavity meanders and the inconsistency of the diameter is readily seen throughout the length of the hole, thereby effectively rendering useless pin gaging as an effective method of in-process laser drilled borehole measurements.

Figure 7:
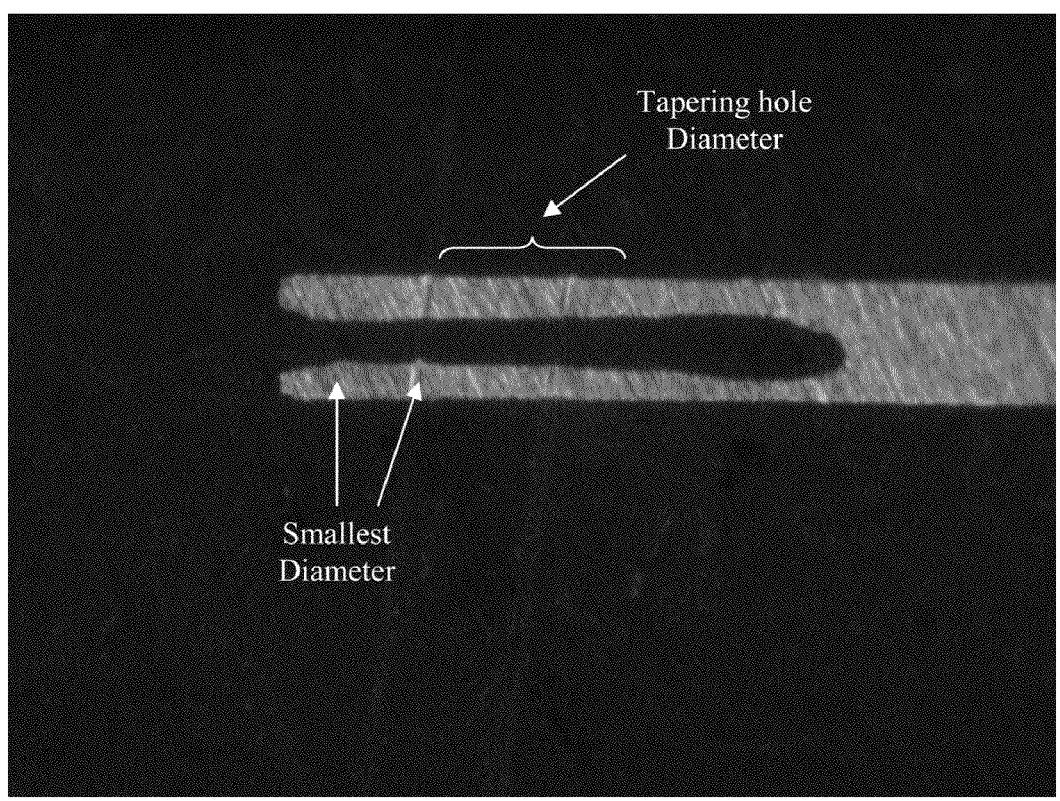
FIG. 7 is a photograph of a mounted and cross-sectioned surgical needle showing that the laser drilled borehole has recast present.

Referring to FIG. 7, a photograph of a cross-sectioned needle shows that the laser-drilled borehole has recast present, as mentioned above, that can influence the pin gaging inspection of the hole diameter of a borehole and may lead to an incorrect conclusion as to the maximum dimensions of the borehole diameter. The bore hole of the needle of FIG. 7 also shows a tapered section just past recast bumps that are seen protruding inwardly from the sides of the borehole. These recast bumps may lead to an incorrect conclusion as to maximum hole diameter and the shape of the bore hole along its length. Note that it is possible to see these anomalies only by cutting the needle in cross-section which also results in the destruction of the needle. Additionally, one must be fortunate to cross-section the needle in the correct plane to reveal such anomalies—often missed due to cross-sectioning. Other than pin gaging, which may be inaccurate and potentially misleading, there are no means available to determine laser drilled borehole diameters, borehole concentricity, and borehole uniformity with a measuring method that is not destructive, however the novel methods of the present invention provide for such determinations.

Given that such hole inconsistencies attendant with laser drilled needles may result in inconsistent needle pulloff (i.e., suture pullout) performance, a non-destructive testing system would provide the ability to 'see' the borehole without destroying the needle, and this would provide the capability to determine beforehand whether or not a needle is suitable for suture attachment or if the attachment method needs to be modified to compensate for the borehole variability.

The novel methods of the present invention provide for the use of X-ray imaging and analysis to evaluate borehole diameters and borehole profiles.

Figure 8:
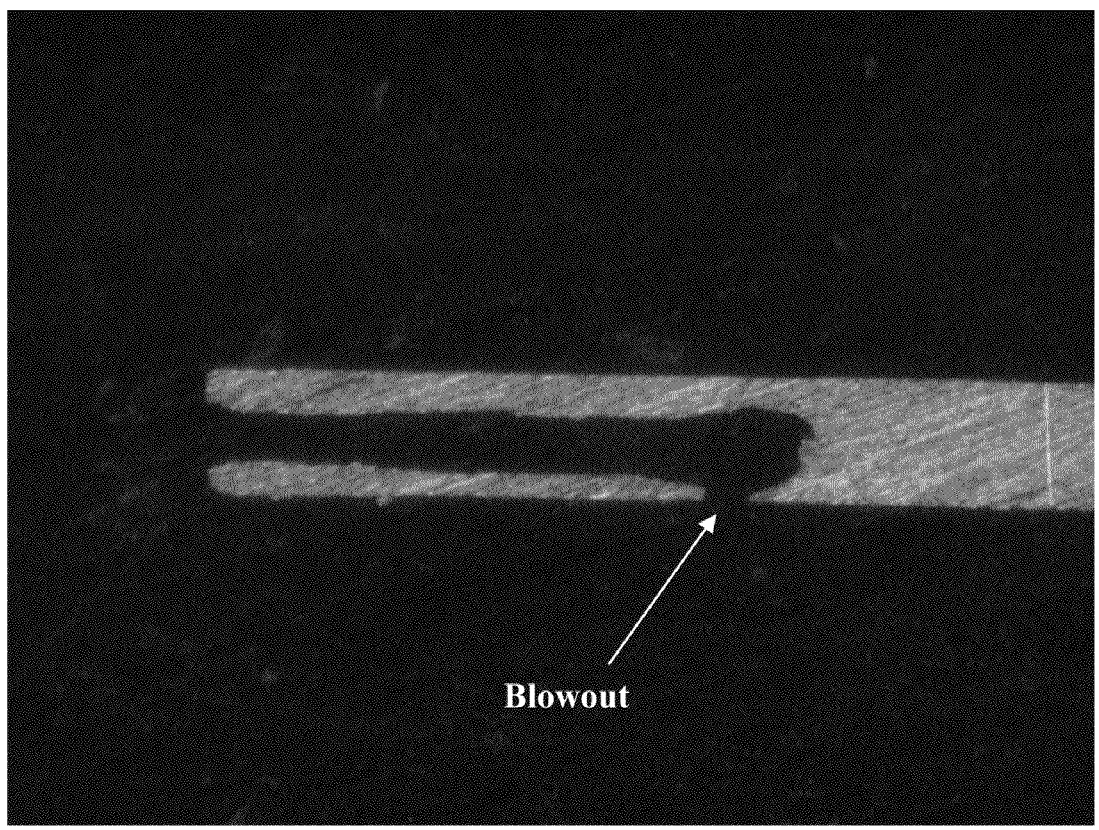
FIG. 8 is a photograph of a mounted cross-section of the proximal end of a laser drilled surgical needle. The drilled bore hole is seen to have a blowout.
Figure 9:
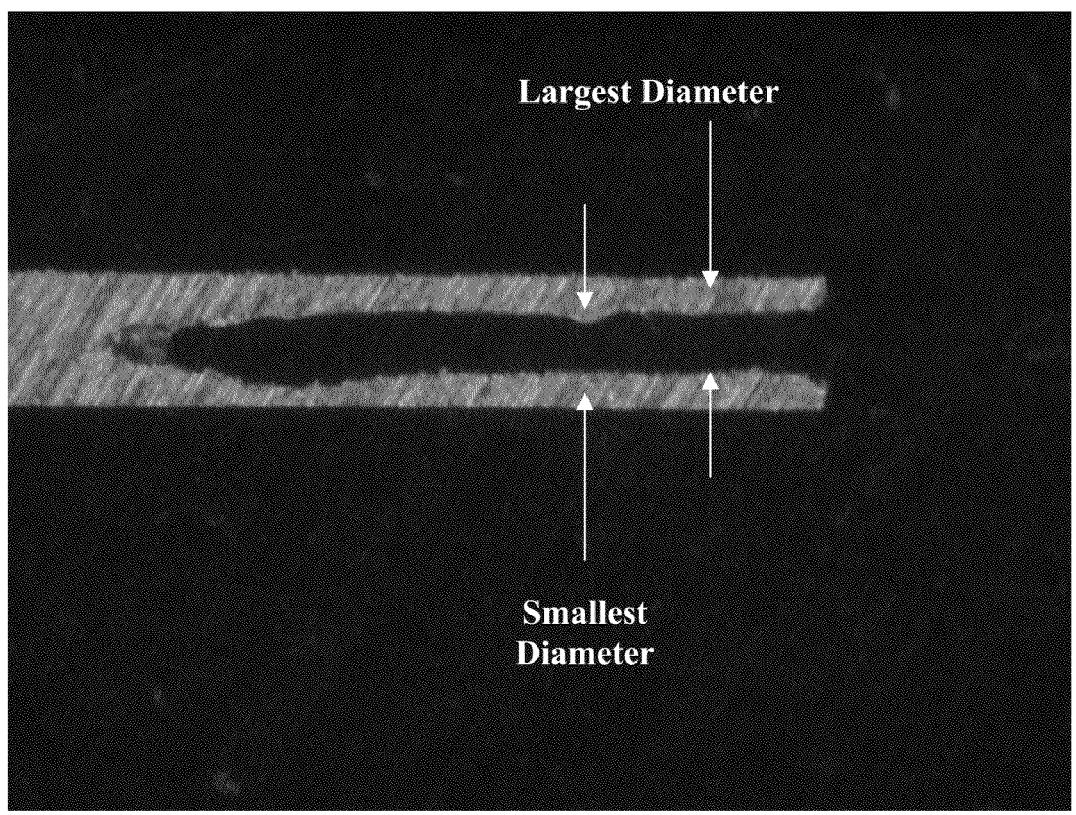
FIG. 9 is a photograph of a mounted cross-section of a proximal end of a laser drilled needle, wherein inconsistencies or variations in borehole diameter are readily visible along the length of the borehole

FIG. 8 is a photo of a mounted cross-section of the proximal end of a laser drilled surgical needle. The drilled bore hole can be seen to have a blowout wherein the laser beam caused the side of the needle surrounding the bore hole to open to the exterior creating a lateral hole or opening in the needle into the borehole cavity. This is undesirable because it creates a cosmetic blemish, can weaken the wall resulting in a potential for breakage, and could create a sharp surface that could cut the user or cut tissue where it is undesired. Referring now to FIG. 9, a photograph of a cross-section of a proximal end of a laser drilled needle is seen. The inconsistencies in borehole diameters are readily visible along the length of the borehole; also seen are the major and minor diameters.

Figure 10:
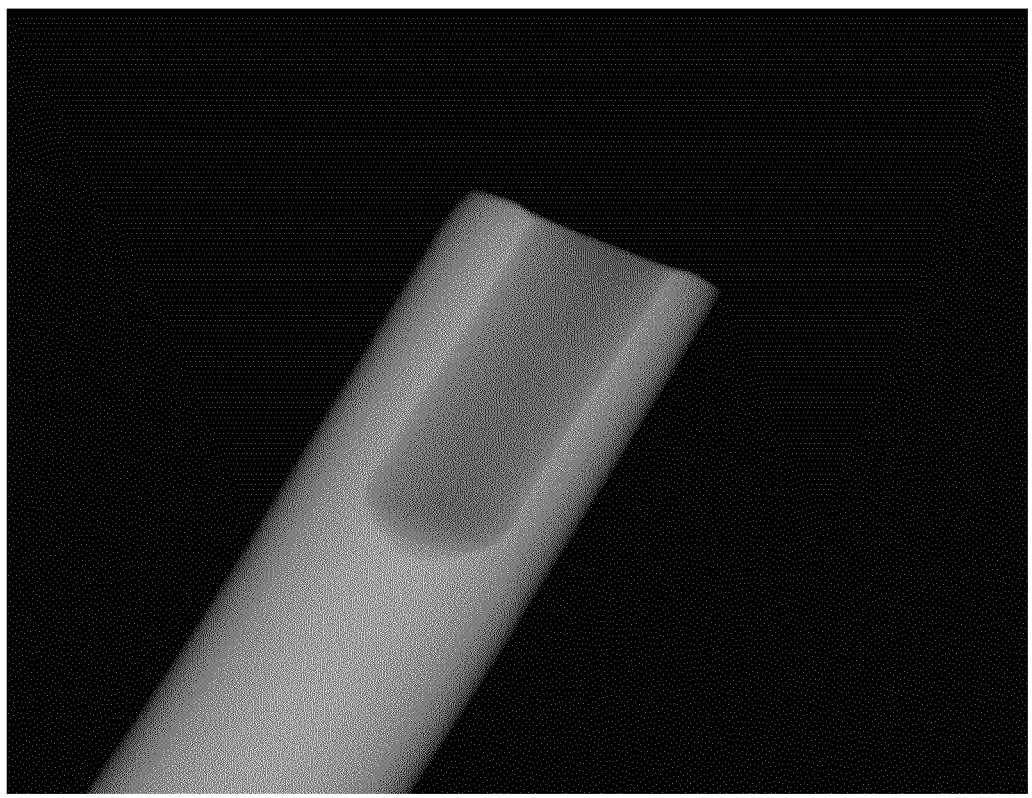
FIG. 10 is a perspective x-ray image of a mechanically drilled surgical needle.
Figure 11:
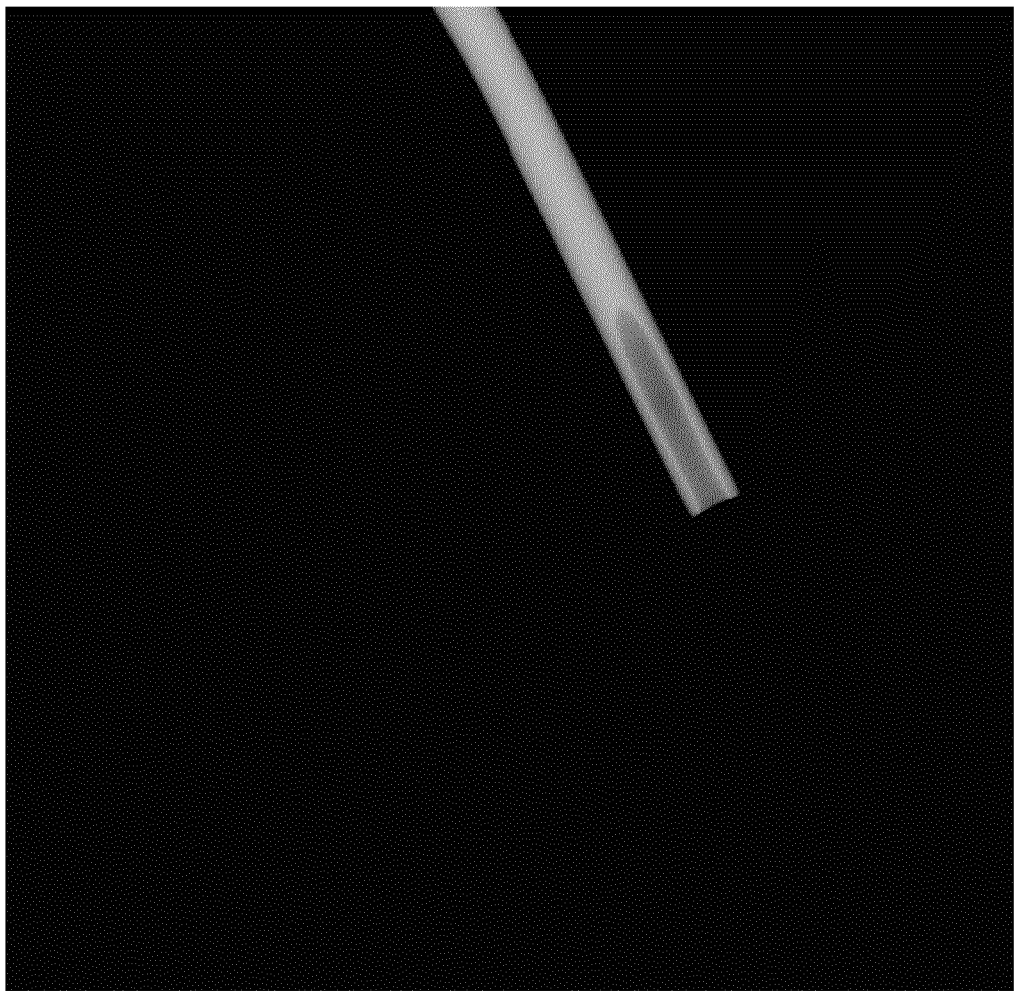
FIG. 11 is a perspective x-ray image of a laser drilled surgical needle.
Figure 12:
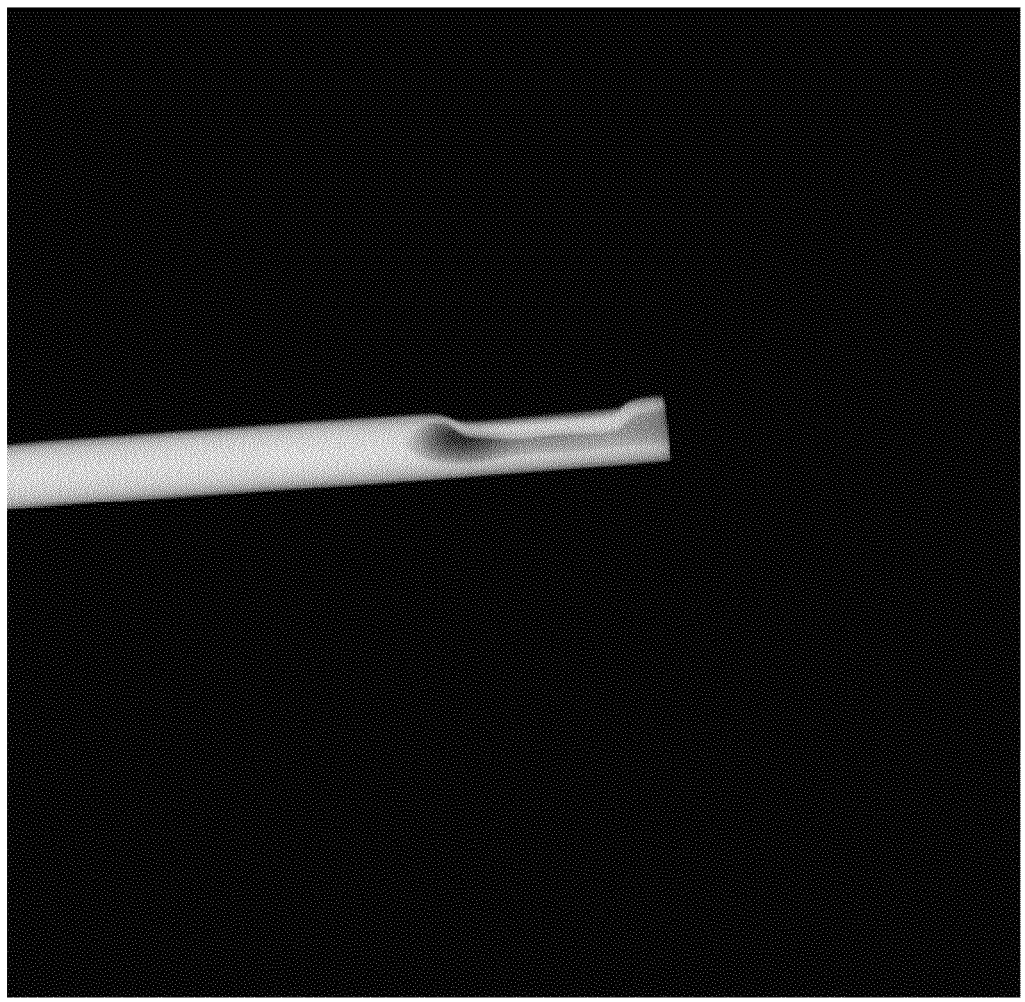
FIG. 12 is an x-ray image of a stake-swaged needle laser drilled needle.

FIGS. 10, 11 and 12 are images illustrating examples of needles that were x-rayed. FIG. 10 shows the distal end of a mechanically drilled needle. The uniformity of the bore hole is readily observed and is seen to be regular in shape as opposed to a laser drilled borehole. FIG. 11 is an x-ray image of the proximal end of a laser drilled needle. The taper of the borehole can be clearly seen. It is apparent that the entire length of the borehole is not available to use due to this taper, whereas in a mechanically drilled needle the entire length of the hole can be utilized (i.e., used for receiving the distal end of a suture).

FIG. 12 is an x-ray image of a stake-swaged needle laser drilled needle. This image illustrates the capability of an x-ray image to present the results of the attachment process, something that cannot be done by any other means that is not destructive.

X-ray imaging is also well suited to manufacturing. Multiple images may be examined and real-time information and evaluation is possible since only a few milliseconds is needed to grab a picture and perform dimensional and profile evaluations; this being dependent upon the x-ray aperture and the computer speed.

One distinct possibility is to couple the picture evaluations to the laser controls and utilize the inspection results to fine tune or control the laser to optimize consistency and minimize variability. One especially significant perspective of x-ray inspection is that it is capable of inspecting wire/hole diameters down to a very small diameter. This is something not achievable pin gaging especially at a high-speed rate. An x-ray system can inspect multiple needles whereas pin gaging can only inspect one needle at a time. Pin gaging is also susceptible to the tolerance of the pins, how much they have worn, their concentricity (not bent from use), and the expertise of the inspector. These traits are all eliminated with x-ray inspection.

It is also impossible to pin gage needles at any significant rate. An x-ray system can inspect at also any rate needed by scanning multiple needles at a time. An x-ray system will also provide instant electronic archival of the results, eliminating paperwork errors and time to transfer data from the measurement to the recording sheet.

Figure 13:
FIG. 13 is an x-ray image of the proximal end of a laser drilled surgical needle in which a potential blowout defect is visible.

FIG. 13 is an x-ray image that depicts a potential blowout condition. This picture shows a needle wherein the laser borehole was drilled off center and the resulting profile has in a thin wall condition where the borehole is almost through the sidewall. This condition can lead to a premature failure of the needle and potential breakage due to the site being a weakened area.

Figure 14:
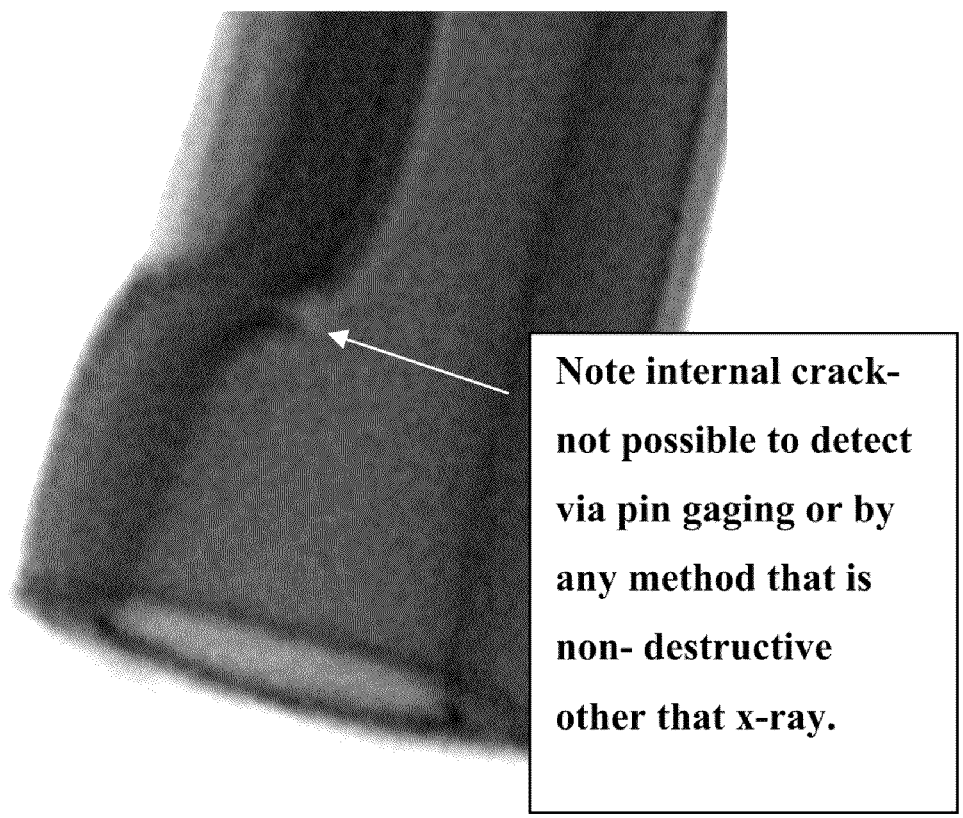
FIG. 14 is a perspective x-ray image of the distal end of a laser drilled surgical needle that has been swaged in which internal cracks resulting from the swaging process are visible.

FIG. 14 is an x-ray image that depicts a needle with a borehole where the needle material has cracked and separated partially. This is a concern in case the crack propagates to the surface resulting in a weakened area that can potentially lead to breakage or the crack may affect a mounted suture such that the suture is cut and fails thus separating from the needle prematurely.

The novel x-ray characterization methods of the present invention provide for a method of characterizing drilled boreholes in automated needle manufacturing processes. They may be utilized with processes that utilize mechanical drilling methods or with processes that utilize laser drilling. The characterization processes of the present invention are particularly preferred for use in laser drilling processes. The x-ray devices or machines that may be utilized in the processes of the present invention will have the following characteristics. The x-ray devices will have the ability to transport and appropriately position individual, or multiple, drilled needles within the x-ray unit between an x-ray emitting source and a sensor. The units will further have the capability to expose the needle(s) to x-rays emitted by the source, and to obtain and digitize resulting x-ray image(s). The units will also be capable of comparing the digitized images to a digital template or series of specific borehole dimensional requirements and provide and generate an instructive disposition signal regarding borehole acceptability. In addition, the units will have processing capability to effectively process the instructive signal to sort or otherwise identify individual needles as to their acceptability, or specific borehole dimensions, and/or to adjust laser parameters to produce boreholes within specified requirements. The x-ray units will be conventional, commercially available units that may be modified for the processes of the present invention, for example, an x-ray unit manufactured by Envision Product Design located in Anchorage, Ak.

The x-ray devices useful in the practice of the processes of the present invention provide a digitized output of the image of a drilled borehole that is compared with the dimensions of a standard. This comparison may be done in several manners including the following manner. The image captured and generated by the x-ray unit is pixilated. These pixels are evaluated for light density. This density is compared to templates that have been likewise pixilated. Since the dimension of a pixel is a known measurement, the system counts the number of pixels within the light density determined by the template and converts this count into a linear measure. If the resulting value is within tolerance or outside of tolerance the appropriate indication is conveyed. Additionally, these measurements may be tracked and statistical conclusions made on an on-going basis for track-and-trend or for statistical control. Further, the information can be optionally placed by inking, laser etching, or other known means upon the needle and/or its carrier for downstream intelligence. In this manner, each characterization for each needle is stored digitally by providing a digital identity for each needle and then storing the image corresponding to the digital identity in a computer database.

Figure 1:
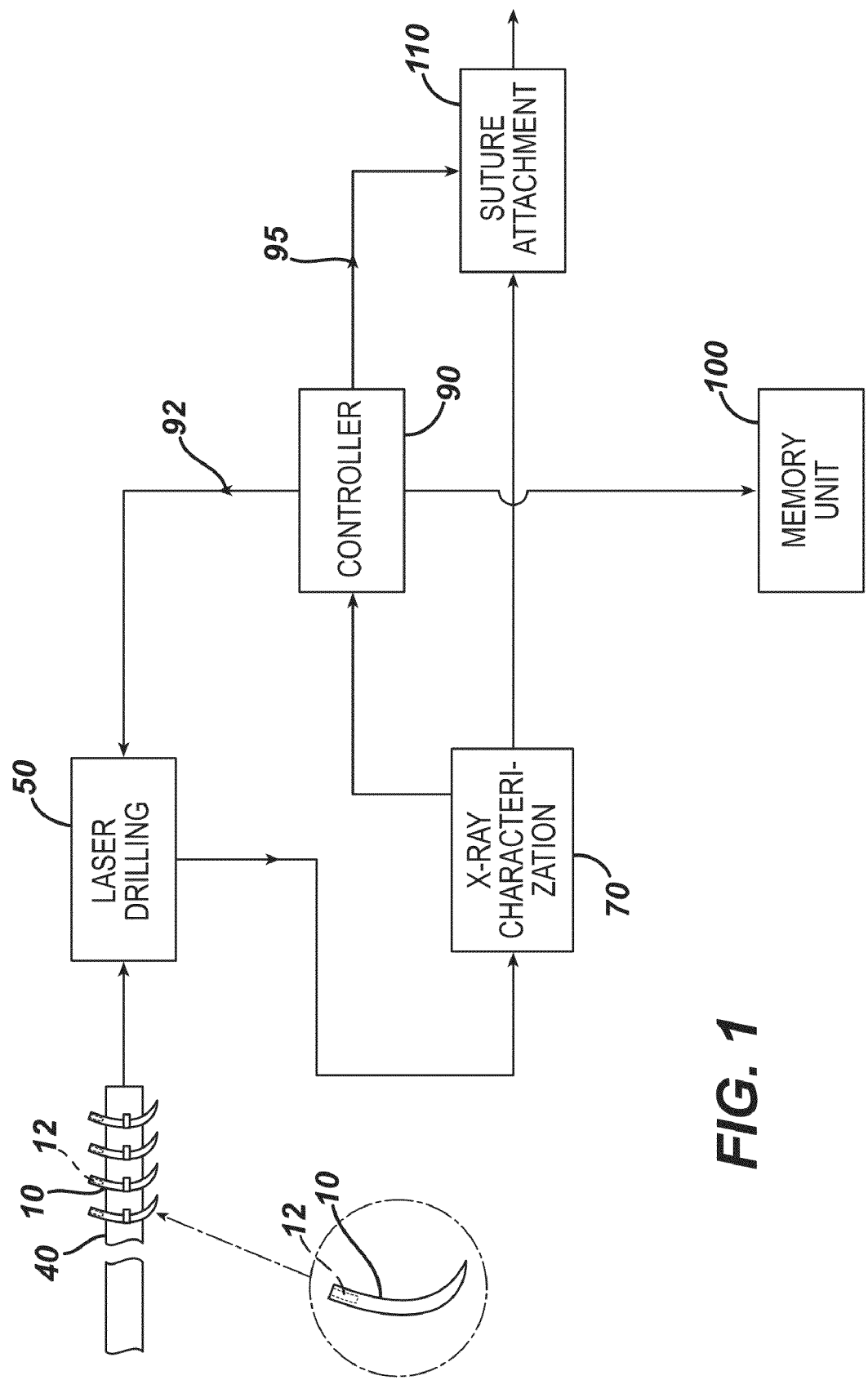
FIG. 1 is a flow diagram of a drilled laser borehole process of the present invention.

A preferred x-ray system that can be used in the practice of the present invention is an integrated inspection system including a shielded cabinet, a 130 kV X-ray source located in the top of the cabinet, a 4"×4" CMOS imaging panel located on an adjustable height platform under the source, a four axis manipulator for positioning a sample under the source, and a computer workstation with software. To image a needle, the process begins with positioning the imaging panel a required distance from the X-ray source, attaching the sample needle to be inspected to the inspection plate on the manipulator, then moving the sample into position based upon the orientation and geometric magnification required. If a previous imaging technique has not been developed, the next step will involve calibration and various test shots to determine the optimum photon energy (voltage or kV) and photon flux (generator current or mA). The optimum kV and mA parameters will be unique to a needle material, thickness and shot geometry and selected to provide the widest possible range of image grayscale values in order to provide the highest possible image contrast. If a previous imaging technique has been developed, then imaging can begin with small adjustments required to orient the needle for viewing an Area of Interest (AOI). In general, shots will involve geometric magnification that results from the needle being located off the imaging panel plane and moved toward the source. As the needle moves closer to the source and away from the imaging panel, the resulting image on the panel will become larger creating a magnified view of the needle. Magnification up to 15× will be possible depending upon the size of the AOI. To acquire an X-ray image the x-ray source is activated, illuminating the needle with an X-ray photon beam that is projected onto the X-ray panel. The needle in the middle of the beam creates a shadow on the panel corresponding to the density of the needle which varies based upon material and geometry or thickness. The panel converts X-ray beam intensity as attenuated by the part into electrical signals corresponding to a range between saturation and no measurable X-ray energy. This signal is digitized into a 12 bit range represented visually by a grayscale value range from 0 to 4096 and presented on an LCD display. Window and leveling tools are then applied to the image to select a narrower range of grayscale values that contain the relevant data, adjusted to maximize the contrast of the image within the range of values of interest. After an image has been acquired and adjusted for best viewing, analysis and interpretation can be completed and the image evaluated based upon inspection requirements. Typical evaluation may include dimensional analysis of features using tools that have been calibrated to the X-ray The novel process of the present invention for characterizing the drilled boreholes in surgical needles is illustrated schematically in FIG. 1. As seen in FIG. 1, surgical needles 10 having laser drilled bore holes 30 in their proximal ends 12 are mounted to strips 40 for moving the needles between production stations. The mounted needles 10 are first moved to laser drilling station 50 where a conventional laser is used having a laser beam with desired waveform and parameters sufficiently effective to drill the boreholes 30 in the proximal ends 20 of the surgical needles 10. Such parameters include conventional parameters, e.g., focal point, pulses and power. The needles 10 and strip 40 are then moved to x-ray characterization station 70. At station 70, each individual needle 10 is x-rayed and a digital characterization of the needle including the borehole 30 in the distal end 12 is obtained. Each needle is given a digital identification number at station 70 and the x-ray characterization is transmitted to controller/processor 90. Controller/processor 90 is a conventional computer or data processor. The characterizations for each needle 10 are stored by controller/processor 90 in memory unit 100, and are analyzed to determine the dimensional characteristics of the borehole including longitudinal orientation, center, maximum and minimum diameter, maximum and minimum length, and maximum and minimum wall thickness about the borehole. The dimensional characteristics are compared to a standard template, and deviations are noted. The characteristics for each needle and deviations from standard are optionally used to generate a signal 92 that is sent back to the laser drilling station 50 to a computer that controls the laser drilling station in order to adjust the characteristics of the laser drilling beam including parameters such as the waveform, pulse, energy, power, focal point, pulses and time to provide for a drilled borehole having a minimal deviation from the specified dimensions. Also optionally, the information related to the borehole dimensions can be used to generate a signal 95 that is sent to a controller/processor for suture attachment system 110, such as a mechanical swaging system, for computing and controlling the attachment pressure and dwell to optimize yields and performance of the suture/needle interface. In this manner, each drilled needle will have a customized set of attachment parameters depending upon the characteristics of the borehole in that needle. Optionally, each needle is marked with a unique identifier; this can be done in a conventional manner including for example, laser etching or ink jet printing. In addition to the identifier (e.g., bar code), the data from the x-ray characterization step for each needle including characteristics and deviations from a standard may optionally be marked on each needle, The surgical needles that can be processed using the novel methods of the present invention include conventional surgical needles having suture mounting ends, preferably with proximal drilled boreholes. The surgical needles can be made from conventional biocompatible materials and equivalents thereof including but not limited to martensitic stainless steel (e.g., UNS 42000), austenitic stainless steel (e.g., UNS 30200), maraging stainless steel (e.g., UNS S45500, UNS 46910, and ETHALLOY brand stainless steel), and refractory alloy systems (e.g., Tungsten-Rhenium) as well as polymeric materials and ceramic materials and composites. The needles may have wire sizes ranging from 1.0 mil to 70 mil, preferably from about 6.0 mil to about 12 mil and will have a variety of conventional lengths. The novel x-ray and laser drilling processes of the present invention have numerous advantages and implications that include the following. x-ray imaging can be performed at the speed of laser drilling in a high speed manufacturing process. The imaging is non-destructive, so that tested needles can be used for finished product. The processes eliminate costly and potentially inaccurate plug gaging. X-ray images can be digitized, magnified, and interrogated by a computer against a profile and/or pre-defined measurements, which can create a realistic measurement and permit informed disposition of every needle manufactured. The x-ray imaging system and process may be linked back to a laser drilling station, whereby the measurements of the borehole are fed back to the laser to make adjustments to fine tune and/or adjust the parameters of the laser beam and thereby control the borehole shape and aspect ratio (depth-to-diameter measurement) by adjusting parameters such as focus, time, energy, pulses, or position. The process of the present invention may be further enhanced to improve quality disposition by marking each needle or the needle carrier adjacent to the needle with a pass/fail or actual measurement in a code or actual numbers for disposition later in the manufacturing process along with a unique digital identity. The data can further be employed to control the process for attaching the suture to the needle (e.g., by conventional swaging processes) through adjustments to pressure, dwell, and closing forces when attaching the needle to suture. This will result in optimized yields and further improved quality of the finished product by ensuring needle/suture attachment integrity.

Although this invention has been shown and described with respect to detailed embodiments thereof, it will be understood by those skilled in the art that various changes in form and detail thereof may be made without departing from the spirit and scope of the claimed invention.

We claim:

1. A method of characterizing a laser drilled borehole in a surgical needle, comprising:
   directing an x-ray beam from an x-ray generator at a proximal end of a surgical needle containing a laser-drilled borehole;
   digitally generating an image of the proximal end of the needle including an image of the borehole from a sensor which the x-ray beam impinges upon, wherein the proximal end of the needle is in between the x-ray generator and the sensor: and,
   processing the digital image to determine a deviation from a standard dimensional specification for the borehole.

2. The method of claim 1 wherein the needle is given a unique digital identifier.

3. The method of claim 1 wherein the deviation is converted to a signal that is sent to a controller.

4. The method of claim 3 wherein the controller computes a signal that is sent to a laser drilling apparatus to modify the parameters of the laser to control the dimensions of the boreholes drilled by the laser drilling apparatus.

5. The method of claim 3, wherein the controller computes a signal for each identified needle that is sent to a swaging apparatus to control the parameters of the swaging apparatus based upon the dimensional measurements of each needle that is characterized.

6. The method of claim 1, wherein the digital image is converted to a pixilated image, and the image is compared to a pixilated template.

7. The method of claim 6, wherein the number of pixels in the image is counted and compared with the number of pixels in the template, and the count is converted into a linear measure.

8. The method of claim 1, wherein the digital image is stored in a database.

9. The method of claim 1, wherein the surgical needle comprises stainless steel.

10. The method of claim 1, wherein the surgical needle comprises a refractory alloy system.

11. The method of claim 10 wherein the refractory alloy system comprises a tungsten-rhenium alloy.

12. The method of claim 1, wherein the digital identifier and the digital image is marked on the needle.

13. The method of claim 1, wherein the needle has a wire size of about 6 mil to about 12 mil.

14. The method of claim 1, wherein a signal is generated based upon the deviation from the dimensional specification and sent to a processor, and the processor computes and sends an output signal to a mechanical swage apparatus to control the swaging of a suture to the borehole of the needle based upon the deviation from the specification.

15. A method of controlling a laser drilling apparatus in a surgical needle borehole drilling process, comprising:
   directing an x-ray beam from an x-ray generator at a proximal end of a surgical needle containing a laser-drilled borehole;
   digitally generating an image of the proximal end of the needle including an image of the borehole from a sensor which the x-ray beam impinges upon, wherein the proximal end of the needle is in between the x-ray generator and the sensor;
   processing the digital image to determine a deviation from a standard dimensional specification for the borehole;
   converting the deviation to a deviation signal that is sent to a controller;
   computing a laser control signal based upon said deviation signal that is sent to a laser drilling apparatus to modify the parameters of the laser beam to control the dimensions of the boreholes drilled by the laser drilling apparatus.

16. The method of claim 15, wherein the parameters of the laser beam that are modified are selected from the group consisting of power, focus, focal point, waveform, pulse, energy and combinations thereof.

17. The method of claim 15, wherein the surgical needle comprises stainless steel.

18. The method of claim 15, wherein the surgical needle comprises a refractory alloy system.

19. The method of claim 18, wherein the refractory alloy system comprises a tungsten-rhenium alloy.

20. The method of claim 15, wherein the needle has a wire size of about 6 mil to about 12 mil.

* * * * *